United States Patent [19]

Collins

[11] Patent Number: 5,464,400

[45] Date of Patent: Nov. 7, 1995

[54] EPIDURAL CONNECTOR

[75] Inventor: Michael N. Collins, Lyminge, England

[73] Assignee: Smiths Industries Public Limited Company, London, England

[21] Appl. No.: 352,145

[22] Filed: Dec. 1, 1994

[30] Foreign Application Priority Data

Dec. 18, 1993 [GB] United Kingdom ............. 9325936

[51] Int. Cl.$^6$ .................................................. A61M 25/00
[52] U.S. Cl. ........................... 604/283; 604/905; 285/322
[58] Field of Search .................................. 604/283, 264, 604/257, 280, 326, 905, 206; 285/31, 32, 322, 323, 324, 358, 397, 398; 411/427, 433

[56] References Cited

U.S. PATENT DOCUMENTS

| | | | |
|---|---|---|---|
| 2,313,780 | 3/1943 | Snyder | 285/322 |
| 2,496,402 | 2/1950 | McVeigh et al. | 285/323 |
| 2,517,689 | 8/1950 | Lement | 285/323 |
| 2,832,598 | 4/1958 | Strub | 285/323 |
| 4,030,741 | 6/1977 | Fidrych | 285/322 |
| 4,187,848 | 2/1980 | Taylor . | |
| 4,250,348 | 2/1981 | Kitagawa | 285/322 |
| 4,252,122 | 2/1981 | Halvorsen | 604/264 |
| 4,559,043 | 12/1985 | Whitehouse et al. | 604/283 |
| 4,842,592 | 6/1989 | Caggiani et al. | 604/283 |
| 4,857,062 | 8/1989 | Russell | 604/905 |
| 5,053,015 | 10/1991 | Gross | 604/283 |
| 5,226,898 | 7/1993 | Gross | 604/283 |

FOREIGN PATENT DOCUMENTS

| | | |
|---|---|---|
| 837661 | 6/1960 | United Kingdom . |
| 1049299 | 11/1966 | United Kingdom . |

*Primary Examiner*—Corrine M. Maglione
*Assistant Examiner*—N. Kent Gring
*Attorney, Agent, or Firm*—Pollock, VandeSande and Priddy

[57] ABSTRACT

An epidural connector has a housing in two parts, one of which contains a resilient, compressible slug with an axial bore into which an epidural cannula is inserted. The slug has a hexagonal external shape with flats separated from one another by rounded corners. The inside of the first part of the housing is of circular shape so that gaps are formed between the slug and the inside of the housing. The second part of the housing is screwed into the rear of the first part and has a female bore for receiving a male coupling. The forward end of the second part of the housing engages the rear end of the slug so that the slug can be compressed about the cannula and deformed into the gaps to accommodate cannulae of different diameters.

9 Claims, 1 Drawing Sheet

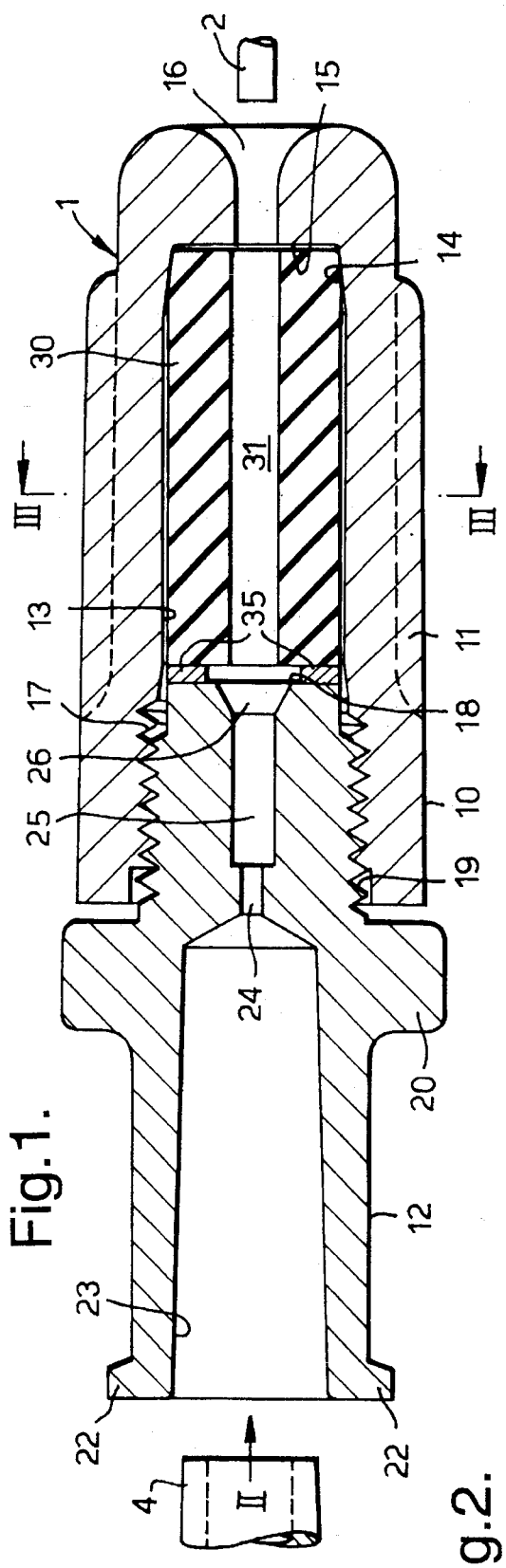
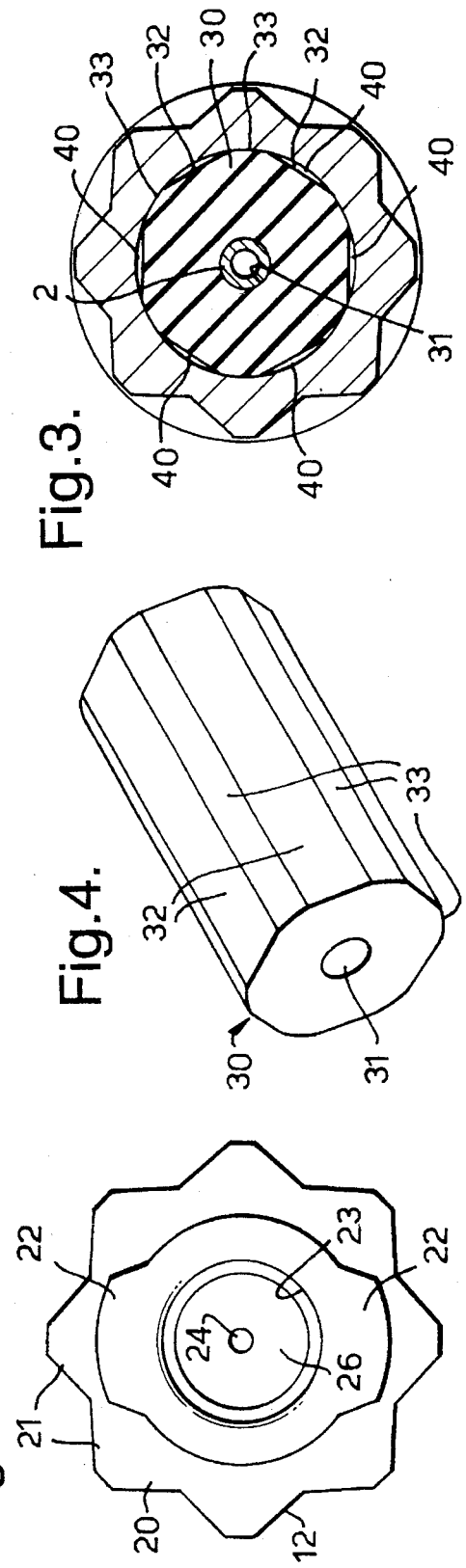

5,464,400

EPIDURAL CONNECTOR

BACKGROUND OF THE INVENTION

This invention relates to connectors.

The invention is more particularly concerned with connectors for connection to the outside of tubes, such as epidural cannulae, and to assemblies including such connectors.

In known epidural cannula connectors, a cannula extends through a bore in a resilient slug. The slug is located between two halves of a housing that are screw threaded with one another. When the two halves of the housing are tightened, they compress the slug axially, thereby causing it to expand radially. The outer surface of the slug engages the inside of the housing and the bore through the slug is squeezed into sealing engagement with the cannula. One half of the housing has a female luer coupling, or other coupling, to which a cooperating connector can be mated. Examples of such connectors are described in U.S. Pat. No. 4,187,848, Brit J. Anaesth (1964) 36, pp 740, 741 and Brit J. Anaesth (1961), 33, pp 664, 665. Epidural connectors are available, such as from Portex Limited of Hythe, Kent, England under reference number 100/382.

One problem with these connectors is that, if they are over-tightened, there is a risk of crushing the cannula because of its small diameter, typically about 1 min. The problem is aggravated if the connector is to be used with cannulae of different diameters since the slug of the connector must be capable of sealing with the smallest of the cannulae, increasing the risk of crushing the larger cannulae.

BRIEF SUMMARY OF THE INVENTION

It is an object of the present invention to provide an improved connector.

According to one aspect of the present invention there is provided a connector for connection to a tube, the connector having a compressible member with a bore therethrough sized to receive the tube, a housing having a first tubular part in which the compressible member is located, the first part having a shoulder at one end for engagement with one end of the compressible member, a second part displaceable axially relative to the first part, the second part having a contact region for engagement with the other end of the compressible member such that, by displacing the first and second parts together, the compressible member can be compressed axially to seal about the tube, the external surface of the compressible member and the internal surface of the first part being so arranged that the compressible member contacts the internal surface at a plurality of locations spaced around the compressible member and separated from one another by gaps into which the compressible member can be deformed.

The external surface of the compressible member may be of non-circular shape and the interior of the first part be of circular shape. The compressible member preferably has a plurality of external flats around it separated from one another by corners, the compressible member contacting the internal surface of the first part at its corners. The compressible member may be of hexagonal shape and the corners of the compressible member may be rounded. The first part is preferably reduced in diameter internally towards the shoulder so that it grips the compressible member in the region of the shoulder prior to displacing the first and second parts together.

According to another aspect of the present invention there is provided an epidural connector assembly including an epidural cannula and a connector according to the above one aspect of the invention. The second part may have a female tapered bore adapted to engage a male tapered coupling.

An epidural connector assembly in accordance with the present invention will now be described, by way of example, with reference to the accompanying drawings.

BRIEF DESCRIPTION OF THE DRAWINGS

FIG. 1 is a sectional side elevation of the connector before mounting on a cannula;

FIG. 2 is an end view of the connector in the direction of the arrow II in FIG. 1;

FIG. 3 is a transverse section along the line III—III of FIG. 1, after assembly on the cannula; and FIG. 4 is a perspective view of the compressible member in the connector.

DETAILED DESCRIPTION OF THE PREFERRED EMBODIMENT

The connector 1 is secured to the rear, machine, or proximal end of an epidural cannula 2 and provides a coupling to which a male luer coupling 4 (such as provided by the nose of a syringe) can be mated to enable the supply of analgesia liquid to the cannula.

The connector 1 has a tubular housing 10 of a rigid polyester material formed as a first, forward part 11 and a separate second, rear part 12. The forward part 11 is ribbed externally and has an hollow recess 13 internally of circular section and with a diameter of 4.97 mm. At the forward end of the recess 13 there is a short tapered section 14, which reduces in diameter along its length, and an annular shoulder 15 surrounding an axial opening 16 of diameter 1.2 mm. The opening 16 is flared outwardly at its forward end to provide a rounded mouth to the opening. The rear end of the recess 13 has an internal screw thread 17 receiving the forward end of the rear part 12 of the housing 10.

The forward end of the rear part 12 has a flat end surface or contact region 18 and an external screw thread 19 that engages with the thread 17 in the forward part 11. An external flange 20 projects radially from the rear part 12 at a point forwardly of the midpoint along its length. The flange 20 has teeth 21 around its edge to enable it to be gripped securely between the fingers. At its rear end, the rear part 12 has two radially-projecting lugs 22, for engagement by the coupling 4, and opens into a female luer taper bore 23 with a diameter of 4.3 mm at its forward end. The bore 23 extends to the region of the flange 20 where it communicates with a short intermediate bore 24 of diameter 0.6 mm. The intermediate bore 24 opens into a larger bore 25 of diameter 1.2 mm, which has a tapered opening 26.

The connector 1 also includes a compressible, resilient member or slug 30, such as of natural or synthetic rubber with a hardness around 50 IRHD. The slug 30 is of generally cylindrical shape being 13.7 mm long and with an axial bore 31 of diameter 1.4 mm. Externally, the slug 30 is of hexagonal shape having six longitudinal flats 32 separated by rounded corners 33 and with a maximum diameter of 4.85 mm. The slug 30 is slightly smaller in diameter than the recess 13 in which the slug is received but is slightly larger than the smaller end of the tapered section 14, so that is gripped at its forward end, close to where it contacts the shoulder 15, prior to the two parts of the housing being displaced towards one another. The rear end of the slug 30 contacts one face of a steel washer 35 the other face of which is contacted by the contact region 18 on the rear part 12 of the housing. The opposite ends of the slug 30 are thereby engaged, either directly or indirectly, by the shoulder 15 and the contact region 18 on the two parts of the housing 10.

In use, the epidural cannula 2 is pushed through the opening 16 and into the bore 31 of the slug 30, in which it is a sliding fit. The rear end of the cannula 2 passes through the washer 35 and into the forward bore 25 of the rear part 12 of the housing. Insertion of the cannula 2 is limited by a step between the forward bore 25 and the intermediate bore 24, the diameter of which is too small for the cannula. The two parts 11 and 12 of the housing 10 are screwed together to compress axially the slug 30. This causes radial expansion of the slug 30 so that its corners 33 contact the inside of the recess 13 and so that the bore 31 is compressed into sealing engagement with the outside of the cannula 2 and grips it sufficiently to prevent it being pulled out of the connector. When tightened to its correct extent, there will be six gaps 40 between the slug 30 and the forward part 11 of the housing in the region of each flat 32. These gaps 40 provide space to accommodate excess material from the slug 30 when it is compressed further. In this way, the material of the slug 30 can be deformed outwardly instead of being deformed inwardly against the cannula 2, which could cause crushing. The male luer coupling 4 can then be inserted into the bore 23 to administer fluid to the cannula 2.

It will be appreciated that the resilient slug 30 could have more flats or fewer flats than the six described above. The slug could be given a non-circular exterior section in other ways than by the flats, such as, for example by giving it grooves or making it of an elliptical shape. Alternatively, the resilient slug could have a circular shape and the recess in the housing could be provided with flats or otherwise be non-circular so that expansion recesses are formed between the resilient slug and the housing.

What I claim is:

1. A connector for connection to a tube, the connector comprising a housing and an elongated compressible member located in said housing, wherein said compressible member has two ends, an external surface and a bore therethrough, said bore being sized to receive the tube, wherein said housing comprises: a first tubular part having a hollow interior in which the compressible member is located, said first part having a shoulder at one end for engagement with one of said ends of the compressible member; and a second part displaceable axially relative to the first part, the second part having a contact region for engagement with another of said ends of the compressible member such that, by displacing said first and second parts together, said compressible member is compressed axially and thereby expands radially into contact with an internal surface of said first part to seal about the tube, and wherein said external surface of said compressible member and said internal surface of the first part are so shaped that said compressible member contacts the internal surface at a plurality of locations spaced around the compressible member, said locations being separated from one another by gaps extending along the length of said compressible member to provide regions into which the compressible member can be deformed.

2. A connector according to claim 1, wherein said external surface of said compressible member is of non-circular shape and the hollow interior of said first tubular part is of circular shape.

3. A connector according to claim 1, wherein said compressible member has a plurality of external flats around it separated from one another by corners, and wherein said compressible member contacts said internal surface of said first part at said corners.

4. A connector according to claim 3, wherein the cross section of said compressible member is of hexagonal shape.

5. A connector according to claim 3, wherein said corners of said compressible member are rounded.

6. A connector according to claim 1, wherein said hollow interior of said first part is reduced in diameter towards said shoulder so that it grips said compressible member in the region of the shoulder prior to displacing said first and second parts together.

7. An epidural connector assembly comprising an epidural cannula and a connector, wherein the connector comprises a housing and an elongated compressible member located in said housing, said compressible member having two ends, an external surface and a bore therethrough, said bore being sized to receive said cannula, wherein said housing comprises: a first tubular part in which the compressible member is located, said first part having a shoulder at one end for engagement with one of said ends of the compressible member; and a second part displaceable axially relative to the first part, the second part having a contact region for engagement with another of said ends of the compressible member such that, by displacing the first and second parts together, the compressible member is compressed axially and thereby expands radially into contact with an internal surface of said first tubular part to seal about the cannula, and wherein said external surface of the compressible member and the internal surface of the first part are so shaped that the compressible member contacts the internal surface at a plurality of locations spaced around the compressible member, said locations being separated from one another by gaps extending along the length of said compressible member to provide regions into which the compressible member can be deformed.

8. An epidural connector assembly according to claim 7, wherein the second part has a female tapered bore shaped to engage a male tapered coupling.

9. An epidural connector assembly comprising an epidural cannula and a connector, wherein the connector comprises a housing and an elongated compressible member located in said housing, said compressible member having two ends, an external surface and a bore therethrough, said bore being sized to receive said cannula, and wherein said housing comprises: a first tubular part in which the compressible member is located, said first tubular part having a shoulder at one end for engagement with one of said ends of the compressible member; and a second part displaceable axially relative to the first part, the second part having a contact region for engagement with another of said ends of the compressible member such that, by displacing said first and second parts together, the compressible member is compressed axially and thereby expands radially into contact with an internal surface of said first tubular part to seal about the cannula, wherein said compressible member has a plurality of external flats around it separated from one another by corners, and wherein said compressible member contacts an internal surface of said first tubular part at its corners so as to define a plurality of gaps extending along the exterior of said compressible member which provide regions between the compressible member and the first tubular part into which the compressible member can be deformed.

* * * * *